(12) United States Patent
Tornier et al.

(10) Patent No.: US 6,334,874 B1
(45) Date of Patent: Jan. 1, 2002

(54) HUMERAL PROSTHESIS

(75) Inventors: Alain Tornier, Saint Ismier; Pascal Boileau, Nice; Gilles Walch, Lyons, all of (FR)

(73) Assignee: Tornier SA, Saint Ismier (FR)

( * ) Notice: Subject to any disclaimer, the term of this patent is extended or adjusted under 35 U.S.C. 154(b) by 0 days.

(21) Appl. No.: 09/590,083

(22) Filed: Jun. 9, 2000

(30) Foreign Application Priority Data

Jun. 9, 1999 (FR) .............................................. 99 07510

(51) Int. Cl.[7] .................................................. A61F 2/40
(52) U.S. Cl. .................................. 623/19.14; 623/19.11
(58) Field of Search ........................... 623/19.11, 19.12, 623/19.13, 19.14

(56) References Cited

U.S. PATENT DOCUMENTS 5,282,865 A    2/1994   Dong

FOREIGN PATENT DOCUMENTS

| EP | 0664108 | 7/1965 |
|----|---------|--------|
| EP | 0821924 | 2/1998 |
| FR | 2755847 | 5/1998 |
| FR | 2763501 | 11/1998 |
| GB | 1292561 | 10/1972 |
| WO | 9415551 | 7/1994 |
| WO | 9522302 | 8/1995 |
| WO | 9815241 | 4/1998 |

OTHER PUBLICATIONS

Craig et al., Integrated Shoulder System Fracture Technique, BIOMET Inc. 1998, Form No. Y–BMT–595/121598/M.*

* cited by examiner

Primary Examiner—Corrine McDermott
Assistant Examiner—Thomas C. Barrett
(74) Attorney, Agent, or Firm—Dowell & Dowell, P.C.

(57) ABSTRACT

A humeral prosthesis including a shaft adapted to be anchored in a medullary canal of humerus, a metaphyseal portion extending upwardly and endwardly from said shaft and being joined at its outer end to a flange which is adapted to support a dome to cooperate with a glenoidal cavity of a shoulder wherein the metaphyseal portion includes an inner part having at least one antero-posterior rib which is structured to provide an anatomical support for humeral tuberosities and which the at least one rib is oriented at an angle of between 45° to 135° with respect to a frontal plane of the prosthesis.

13 Claims, 4 Drawing Sheets

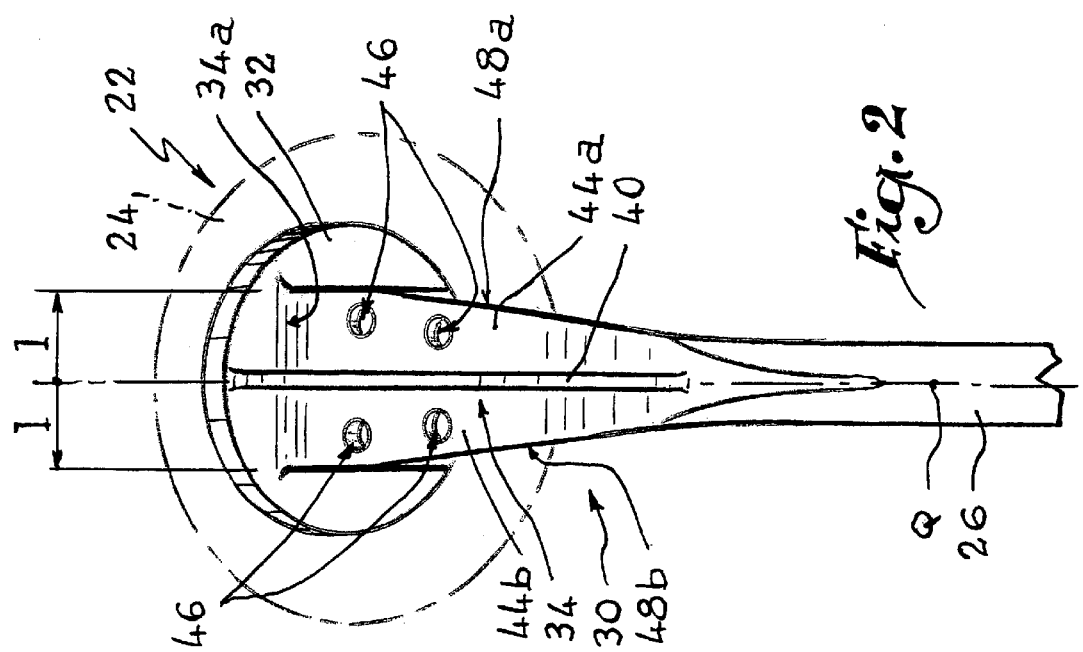
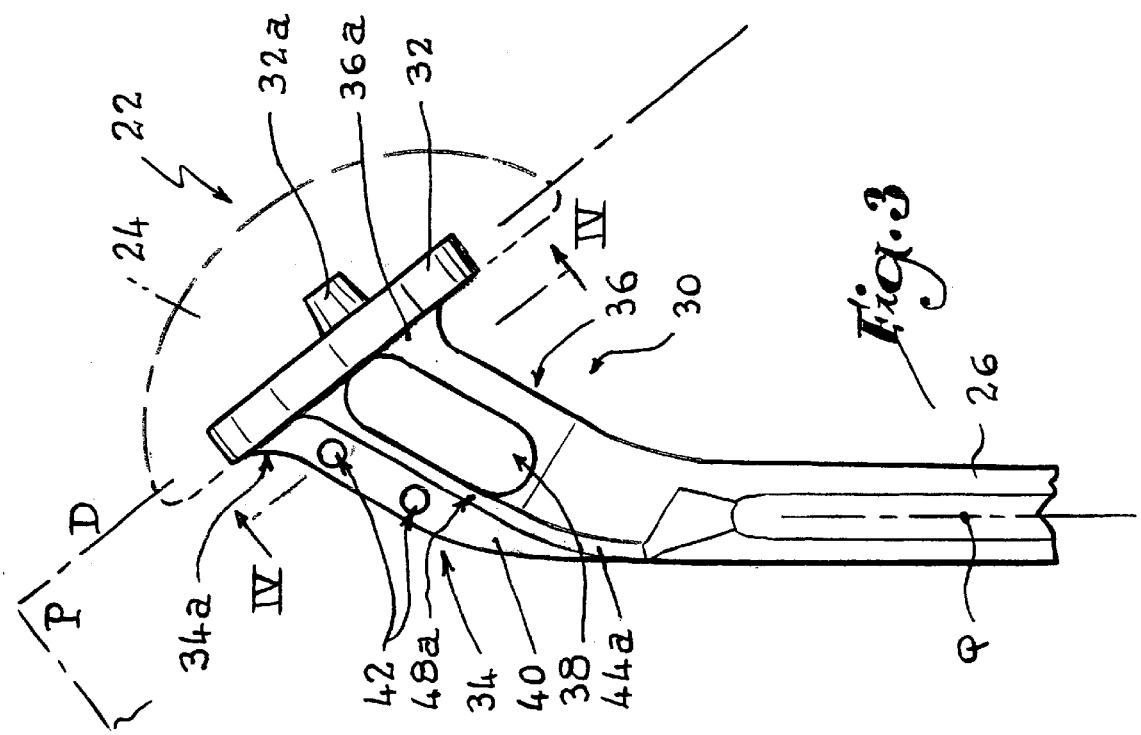

HUMERAL PROSTHESIS

FIELD OF THE INVENTION

The present invention relates to a humeral prosthesis.

BACKGROUND OF THE INVENTION

When there is a fracture of the upper end of a humerus, the latter generally breaks into several pieces, namely the diaphysis, the humeral tuberosities and, finally, the head of the humerus which cooperates with the glenoidal cavity of the shoulder.

When such a fracture is reduced, only the humeral head has to be replaced by a substantially hemispherical dome, while the other fractured pieces may be reconstituted around a prosthesis.

It is known that such a prosthesis generally comprises a shaft, or diaphyseal portion, introduced in the humeral canal of the diaphysis of the bone. This shaft is extended by a metaphyseal portion which, with reference to a prosthesis borne by a patient standing up, is curved upwardly and inwardly, and around which the tuberosities constituting the metaphysis of the bone are grouped together, with a view to reconstitution thereof. The metaphyseal portion of the prosthesis is joined to a flange for receiving the dome replacing the humeral head.

However, this type of prosthesis presents a drawback, in that it does not allow optimum positioning of the large and small tuberosities with a view to suture thereof.

In order to overcome this drawback, WO-A-98/15241 provides a humeral prosthesis presenting means for positioning these humeral tuberosities. To that end, the zone of connection between the metaphyseal portion of the prosthesis and the flange is provided, in its outer part, with at least one rib extending, with respect to the plane of symmetry of this prosthesis, at an angle included between 20 and 40°. Such a rib, which may be divided into two, extends in the direction of the bicipital groove, in the vicinity of which the large and small tuberosities must be joined. However, such a solution is not completely satisfactory, from the anatomical standpoint, as it is not certain that the humeral tuberosities can be positioned in their natural configuration.

In order to overcome all the drawbacks of the prior art set forth hereinabove, the invention proposes to provide a humeral prosthesis allowing a precise and anatomical positioning of the large and small tuberosities to permit the suturing thereof.

SUMMARY OF THE INVENTION

To that end, the invention relates to a humeral prosthesis comprising a shaft intended to be anchored in the medullary canal of a humerus, a metaphyseal portion extending this shaft upwardly and inwardly, this metaphyseal portion being joined to a flange supporting a dome adapted to cooperate with the glenoidal cavity of the shoulder, characterized in that the metaphyseal portion comprises, in its outer part, at least one antero-posterior rib for support of the humeral tuberosities, the or each rib extending in a plane oriented at an angle included between 45 and 135° with respect to the frontal plane of the prosthesis.

Thanks to the invention, and in particular to the orientation and dimensions of the or each antero-posterior rib, the humeral tuberosities can be reconstituted around the outer part of the metaphyseal portion of the prosthesis in a satisfactory configuration from the anatomical standpoint. In particular, the angle of orientation of the plane of the or each antero-posterior rib with respect to the frontal plane of the prosthesis may be provided to be close to 90°. This configuration proves particularly advantageous for reconstituting the humeral metaphysis.

According to advantageous aspects of the invention, the prosthesis incorporates one or more of the following characteristics:

The or each antero-posterior rib extends, from the frontal plane, with a maximum width such that its projection on a plane perpendicular to the frontal plane corresponds substantially to the distance separating the posterior edge of the bicipital groove of the humeral metaphysis with respect to a central axis of the humeral head. The width of the or each antero-posterior rib is thus adapted to the anatomy of the humeral metaphysis.

The metaphyseal portion further comprises, in its outer part, an outer median rib extending substantially along said frontal plane, the or each antero-posterior rib extending from the inner edge of said outer median rib. This configuration allows a particularly satisfactory bearing for the humeral tuberosities.

The metaphyseal portion of the prosthesis comprises two antero-posterior ribs, substantially symmetrical to each other with respect to the frontal plane. These ribs make it possible to use the prosthesis of the invention for a right or left shoulder and give this metaphyseal portion a good dimensional stability, particularly in torsion.

The metaphyseal portion comprises two branches, outer and inner respectively, defining therebetween a recess, the outer branch being provided with the or each antero-posterior rib. This recess allows osseous fusion through the metaphyseal portion of the prosthesis.

The outer branch is formed by said outer median rib and said two antero-posterior ribs. This embodiment is advantageous since it is of simple construction and it allows the prosthesis to present a wide outer surface for contact with the humeral tuberosities. In that case, the outer branch advantageously presents a T-shaped cross-section.

The free edge of the or each rib is inclined with respect to the frontal plane, the width of the or each rib increasing in the direction of the flange.

BRIEF DESCRIPTION OF THE DRAWINGS

The invention will be more readily understood on reading the following description given by way of non-limiting example, with reference to the accompanying drawings, in which:

FIGS. 2 and 3 are respectively front and side views of a humeral prosthesis according to the invention.

DESCRIPTION OF PREFERRED EMBODIMENT

Figure 1:
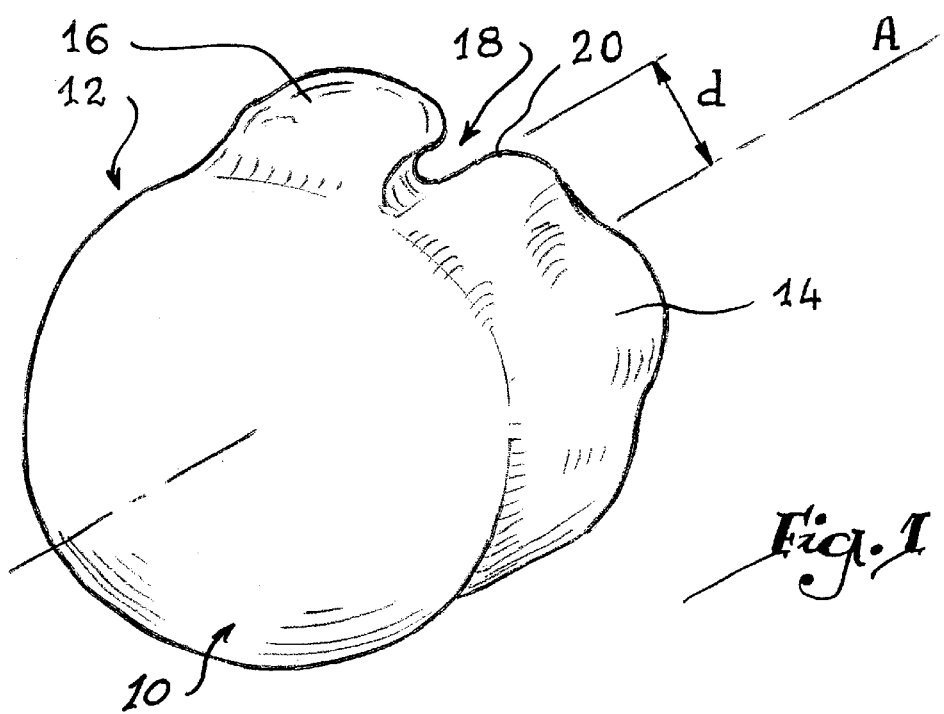
FIG. 1 is a schematic plan view showing the upper end of a humerus.

Referring now to the drawings, FIG. 1 shows the upper end of a humerus 10 which comprises a metaphyseal portion surmounted by a humeral head 12 cooperating with the glenoidal cavity of the shoulder (not shown). On the metaphyseal portion are formed a large tuberosity 14 and a small tuberosity 16 which define therebetween a so-called bicipital groove 18.

When the humerus 10 is fractured, the posterior edge 20 of the groove 18, adjacent the large tuberosity 14, often constitutes the starting point of such a fracture. A denotes the central axis of the humeral head 12, and d the distance separating this axis A and the posterior edge 20 of the groove 18. Axis A is determined, in known manner, in accordance with a method described in the article "Anatomic determination of humeral head retroversion: the relationship of the central axis of the humeral head to the bicipital groove", extracted from the publication "Journal of Shoulder and Elbow Surgery", in the September–October 1993 number.

Figure 4:
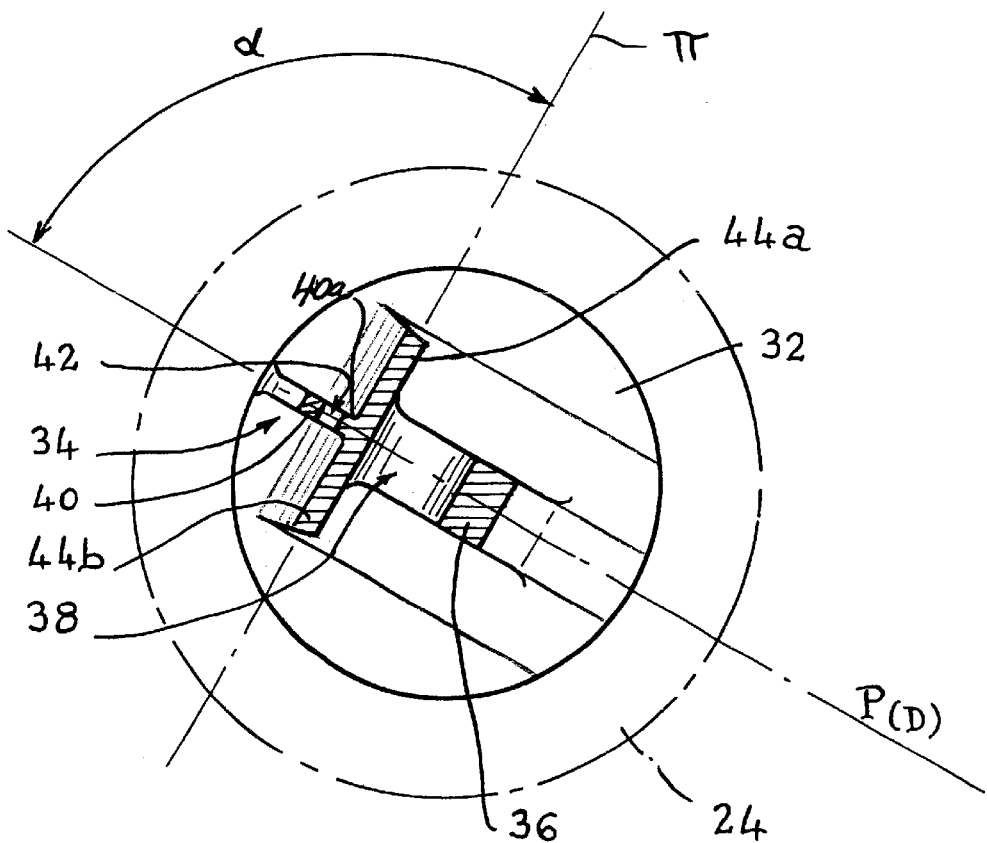
FIG. 4 is a section along line IV—IV in FIG. 3.

FIGS. 2 to 4 show a prosthesis according to the invention, generally designed by reference 22. The terms lower, upper, inner, outer, anterior and posterior used hereinafter must be understood as referring to a prosthesis borne by a patient standing up.

The prosthesis 22 is intended to support a substantially hemispherical dome 24 adapted to cooperate with the glenoidal cavity of a patient's shoulder.

Figure 5:
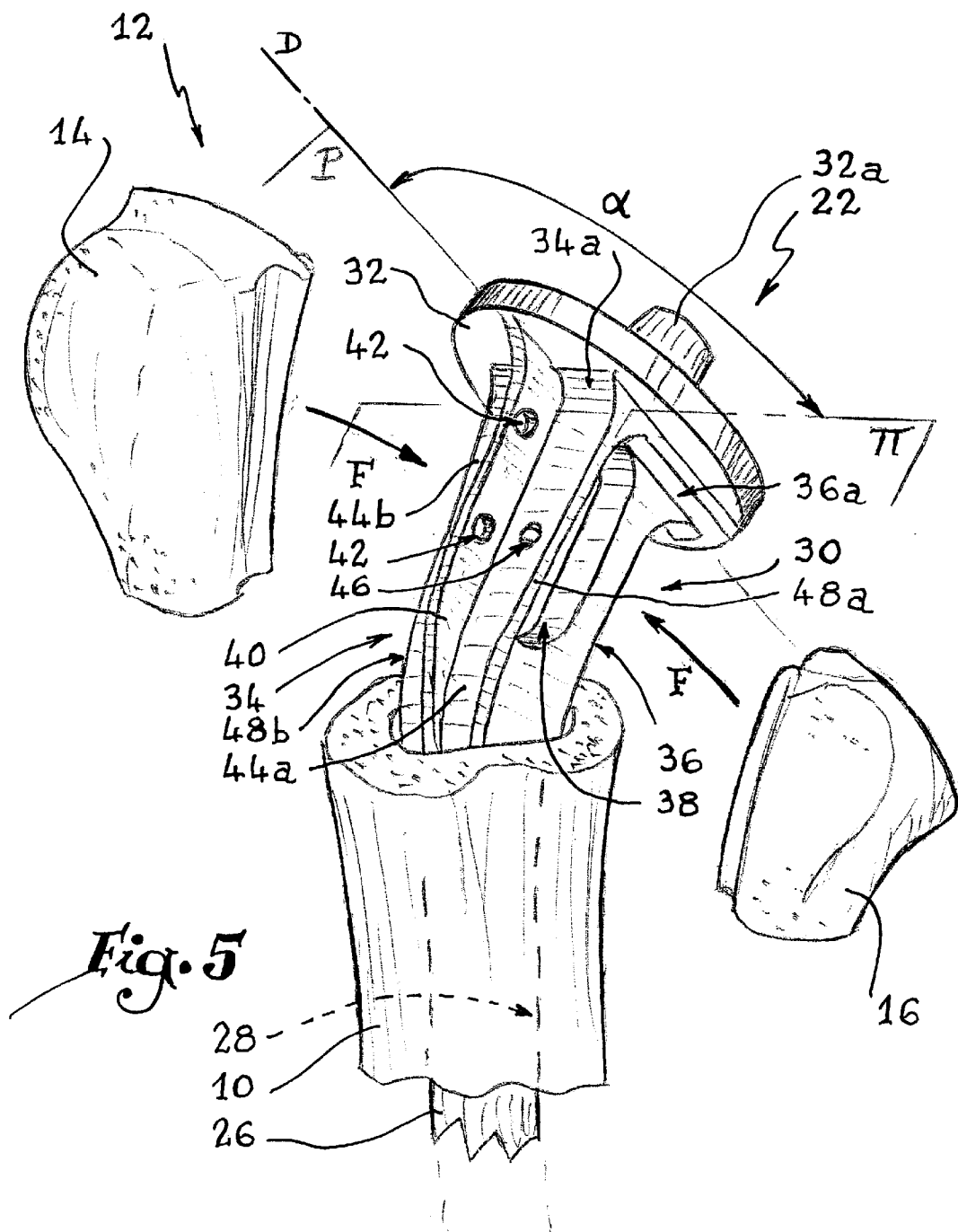
FIG. 5 is a view in perspective illustrating the prosthesis of FIGS. 2 and 3 implanted in the medullary canal of a humerus, and humeral tuberosities arranged in the vicinity of this prosthesis.

This prosthesis comprises a shaft 26 of substantially circular cross-section, intended to engage in the humeral canal 28 as shown in particular in FIG. 5. This shaft 26 is extended by a metaphyseal portion 30 to which is joined a flange 32 adapted to be removably connected to the dome 24 thanks to a lug 32a.

The frontal plane P of the prosthesis is the plane containing the central axis Q of the shaft 26 and a median axis or diameter D of the flange 32. Plane P is perpendicular to the plane of FIG. 2 and its trace merges with that of axes D and Q in this Figure. Plane P is parallel to the plane of FIG. 3. In practice, plane P is a plane of symmetry of the prosthesis 22.

The metaphyseal portion 30 comprises outer and inner parts, namely an outer branch 34 and an inner branch 36 which are each joined to the lower face of the flange 32, by respective connection zones 34a and 36a. These latter are located substantially along axis D. Once the prosthesis is implanted, axis D of the flange is superposed on the central axis A of the humeral head 12.

Between the branches 34 and 36 there is defined a recess 38 constituting a free volume for bringing together and fusion of the fragments of bone of the metaphysis. The existence of this free volume allows the formation of an osseous bridge ensuring efficient anchoring of this prosthesis in the humerus.

The inner branch 36 presents a rectangular cross-section which is substantially constant over the whole length of this branch.

The outer branch 34 comprises an outwardly projecting median rib 40 whose thickness is clearly less than that of the inner branch 36. This outer median rib 40 extends substantially along the frontal plane P. It is pierced with orifices 42 intended for the passage of the suture threads.

Two antero-posterior ribs 44, namely a rear lateral rib 44a and a front lateral rib 44b each extend, from the inner edge 40a of the median rib 40, along a plane π of which α denotes the angle of orientation with respect to the frontal plane P. Angle α is about 90°, i.e. the antero-posterior ribs 44 are substantially perpendicular to the median rib 40. As is visible in FIG. 4, the outer branch 34 therefore presents a T-shaped cross section.

The antero-posterior ribs 44 allow an anatomic repositioning of the tuberosities 14 and 16 and of the bicipital groove 18 thanks to bearing on at least one of the ribs, as represented by arrows F in FIG. 5.

Although the value of 90° is particularly advantageous, satisfactory results were able to be obtained with antero-posterior ribs extending in a plane-π of which the angle with respect to the frontal plane is included between 45 and 135°.

Each of the antero-posterior ribs 44a and 44b is pierced with orifices 46 allowing passage of suture threads.

As is illustrated in particular in FIG. 2, the width of the antero-posterior ribs 44 increases towards the flange 32. The respective free edges 48a and 48b of the ribs 44a and 44b diverge from the outside towards the inside of the shoulder, i.e. are inclined with respect to the frontal plane P. The maximum width l of the ribs 44 is equal to the distance d separating the central axis A of the humeral head 12 and the posterior edge 20 of the bicipital groove 18.

In effect, in order to effect synthesis of the humeral tuberosities, the surgeon has a reference in the vertical direction, as the top of the greater tuberosity must lie slightly below the head of the prosthesis. Now, the greater tuberosity may rotate about the axis of the dome. The invention provides the surgeon with a reference to enable him to position the greater tuberosity correctly. This reference is the theoretical position of the bicipital groove 18, determined by the maximum width l of the antero-posterior ribs. This width corresponds in effect to the average anatomical distance measured between the central axis A and the posterior edge 20 of the bicipital groove 18.

Figure 6:
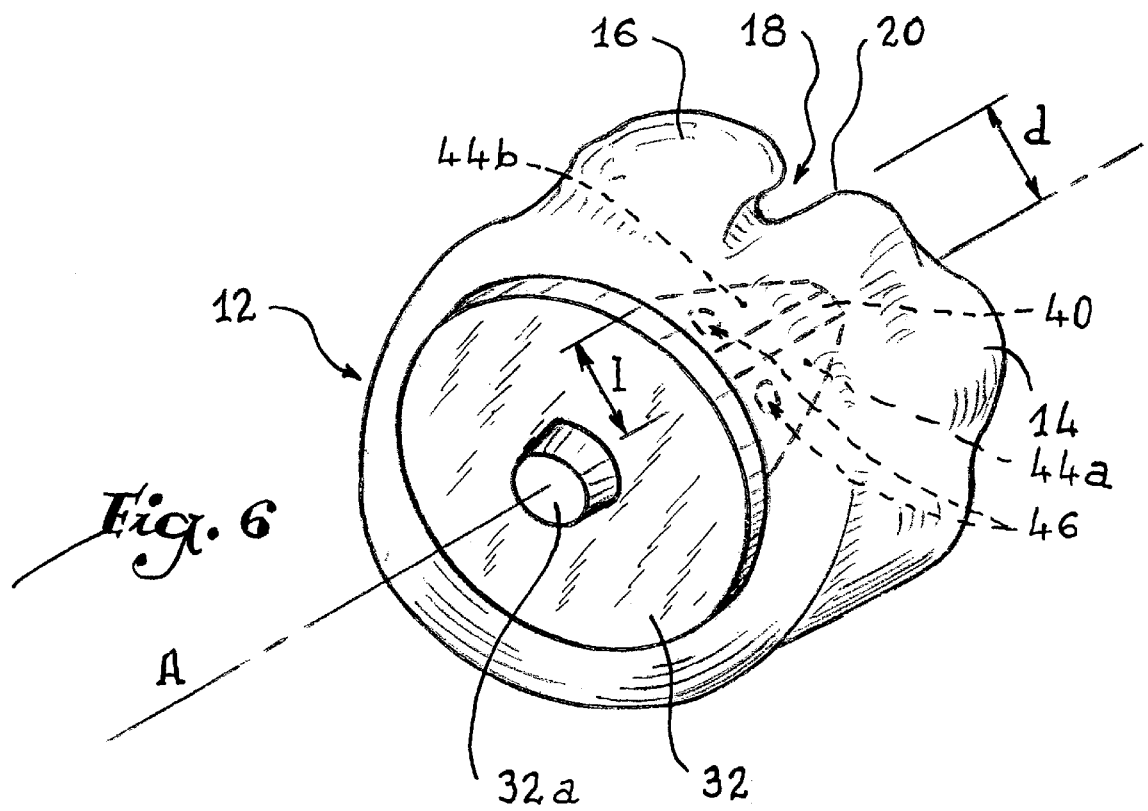
FIG. 6 is a plan view, similar to FIG. 1, illustrating the prosthesis once implanted, the dome for bearing on the glenoidal cavity having been omitted.

Once the prosthesis 22 has been positioned and the humeral tuberosities 14 and 16 joined in the vicinity of this prosthesis, as shown in FIG. 6, osseous fusion can take place, such fusion resulting in an anatomical reconstitution of the bone.

The width of the ribs, and in particular their maximum width l may be adapted as a function of the size of the prosthesis, i.e., in particular, of the position of the bicipital groove. In practice, this width l is included between 5.5 and 13 mm and three sizes of prostheses can be provided, of which the antero-posterior ribs present a maximum width l equal to 6, 9 or 12 mm respectively.

In the case of the ribs 44a and 44b not being perpendicular to the frontal plane, their maximum width l is chosen so that the projection thereof on a plane perpendicular to this frontal plane corresponds to the distance d. In the case shown in the Figures, the width l is equal to their projection on the plane π.

What is claimed is:

1. Humeral prosthesis, including a shaft adapted to be anchored in a medullary canal of a humerus, a metaphyseal portion extending from said shaft upwardly and inwardly, said metaphyseal portion being joined to a flange which is adapted to support a dome adapted to cooperate with a glenoidal cavity of a shoulder, wherein said metaphyseal portion includes along an outer part thereof, at least one antero-posterior rib adapted to anatomically support humeral tuberosities, and said at least one antero-posterior rib extending in a plane oriented at an angle( ) included between 45° and 135° with respect to a frontal plane (P) of the prosthesis and at an angle inwardly relative to an elongated axes (Q) of said shaft.

2. The prostheses of claim 1, wherein the angle of orientation of the plane of said at least one antero-posterior rib with respect to said frontal plane is approximately 90°.

3. The prosthesis of claim 1, wherein said at least one antero-posterior rib extends, from said frontal plane, with a maximum width such that a projection of said at least one antero-posterior rib on a plane perpendicular to said frontal plane corresponds substantially to a distance separating a posterior edge of a bicipital groove of a humeral metaphysis with respect to a central axis of a humeral head.

4. The prosthesis of claim 1, wherein said outer part of said metaphyseal portion includes an outer median rib extending substantially along said frontal plane, and said at least one antero-posterior rib extending from an inner edge of said outer median rib.

5. The prosthesis of claim 4, wherein said metaphyseal portion comprises two branches, outer and inner respectively, defining therebetween a recess, said outer branch being formed by said outer median rib and by two antero-posterior ribs which are substantially symmetrical to each other with respect to said frontal plane.

6. The prosthesis of claim 5, wherein said outer branch is substantially T-shaped in cross-section.

7. The prosthesis of claim 1, wherein said metaphyseal portion includes two antero-posterior ribs, substantially symmetrical to each other with respect to said frontal plane.

8. The prosthesis of claim 1, wherein the metaphyseal portion comprises two branches, outer and inner respectively, defining therebetween a recess, the outer branch being provided with said at least one antero-posterior rib.

9. The prosthesis of claim 1, wherein a free edge of said at least one antero-posterior rib is inclined with respect to said frontal plane, and a width of said at least one rib increasing in a direction of said flange.

10. The prosthesis of claim 9 in which said metaphyseal portion includes two antero-posterior ribs which are substantially symmetrical to one another with respect to said frontal plane.

11. The prosthesis of claim 10 wherein each of said antero-posterior ribs has a maximum width such that a project of each antero-posterior rib on a plane perpendicular to said frontal plane corresponds substantially to a distance separating a posterior edge of a bicipital groove of a humeral metaphysis with respect to a central axis of a humeral head.

12. The prosthesis of claim 11 wherein said metaphyseal portion includes an outer branch and an inner branch defining a recess therebetween, said outer branch including an outer median rib which extends substantially along said frontal plane and said antero-posterior ribs extending outwardly from an inner edge of said outer median rib and an on opposite sides thereof.

13. The prosthesis of claim 12 in which said antero-posterior ribs extend outwardly in a plane oriented at an angle ( ) of approximately 90°.

* * * * *